US009316648B2

(12) United States Patent
Stephens

(10) Patent No.: US 9,316,648 B2
(45) **Date of Patent: *Apr. 19, 2016**

(54) UREA-BASED SYNTHETIC URINE AND METHOD OF MANUFACTURING SAME

(71) Applicant: Spectrum Laboratories, LLC, Cincinnati, OH (US)

(72) Inventor: James Matthew Stephens, Cincinnati, OH (US)

(73) Assignee: Spectrum Laboratories, LLC, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,642

(22) Filed: Aug. 4, 2015

(65) Prior Publication Data

US 2015/0338414 A1 Nov. 26, 2015

Related U.S. Application Data

(63) Continuation of application No. 14/270,546, filed on May 6, 2014, now Pat. No. 9,128,105.

(60) Provisional application No. 61/819,775, filed on May 6, 2013.

(51) Int. Cl.

| | |
|---|---|
| ***G01N 33/493*** | (2006.01) |
| ***G01N 33/70*** | (2006.01) |
| ***G01N 33/62*** | (2006.01) |

(52) U.S. Cl.

CPC .............. *G01N 33/62* (2013.01); *G01N 33/493* (2013.01); *G01N 33/70* (2013.01); *G01N 2496/80* (2013.01); *Y10T 436/10* (2015.01); *Y10T 436/147777* (2015.01); *Y10T 436/171538* (2015.01)

(58) Field of Classification Search

CPC ..... G01N 31/00; G01N 33/48; G01N 33/487; G01N 33/493; G01N 33/62; G01N 33/70; Y10T 436/10; Y10T 436/108331; Y10T 436/147777; Y10T 436/17; Y10T 436/171538; Y10T 436/25; Y10T 436/2525

USPC ................. 436/8, 18, 98, 106, 108, 174, 176; 252/408.1; 424/545

See application file for complete search history.

(56) References Cited

U.S. PATENT DOCUMENTS

| | | | | |
|---|---|---|---|---|
| 4,146,644 | A | 3/1979 | Griffith | |
| 5,036,014 | A | 7/1991 | Elsohly et al. | |
| 5,328,954 | A | 7/1994 | Sarangapani | |
| 5,489,281 | A | 2/1996 | Watanabe et al. | |
| 6,306,422 | B1 | 10/2001 | Batich et al. | |
| 6,716,632 | B1 * | 4/2004 | Dorn | A01N 47/44 252/380 |
| 7,109,035 | B2 * | 9/2006 | Haddad | G01N 33/94 436/159 |
| 7,192,776 | B2 | 3/2007 | Stephens | |
| 8,148,156 | B1 * | 4/2012 | Daniel | A61L 15/56 252/408.1 |
| 2011/0171074 | A1 * | 7/2011 | Nakao | B32B 25/08 422/120 |
| 2013/0234071 | A1 * | 9/2013 | Deneau | G01N 33/62 252/408.1 |
| 2014/0329327 | A1 | 11/2014 | Stephens | |

OTHER PUBLICATIONS

Kool et al. Soil Biology & Biochemistry, vol. 38, 2006, pp. 1021-1027.*

* cited by examiner

*Primary Examiner* — Maureen Wallenhorst

(74) *Attorney, Agent, or Firm* — McDonald Hopkins LLC

(57) ABSTRACT

A synthetic urine solution and method of its manufacture are disclosed. The solution includes water having a pH between about 3 and about 10. The solution further includes creatinine, a means for removing bacteria from the solution so as to control or eliminate sepsis of the urine solution, preferably through the use of a biocide, and a urea-based compound. The solution exhibits a specific gravity of from 1.005 g/cm$^3$ to 1.025 g/cm$^3$. Additional compounds may also be included to further enhance the aesthetics or apparent authenticity of the synthetic urine.

13 Claims, No Drawings

UREA-BASED SYNTHETIC URINE AND METHOD OF MANUFACTURING SAME

CROSS-REFERENCE TO RELATED APPLICATIONS

This application is a continuation of U.S. patent application Ser. No. 14/270,546, filed May 6, 2014, now U.S. Pat. No. 9,128,105, issued on Sep. 8, 2015 and claims priority to U.S. Provisional Application No. 61/819,775 entitled "UREA-BASED SYNTHETIC URINE AND METHOD OF MANUFACTURING SAME," filed on May 6, 2013, both of which are hereby incorporated by reference in their entireties.

BACKGROUND OF THE INVENTION

This invention relates to a composition and method of manufacturing urea-based synthetic urine. More specifically, the synthetic urine includes biocides to allow for increased shelf stability.

An example of a method of manufacturing synthetic urine may be seen by reference to U.S. Pat. No. 7,192,776, the disclosure of which is hereby incorporated by reference in its entirety.

The kidneys remove unwanted substances circulating in the blood by way of producing urine, which is excreted from the body. Consequently, diverse waste substances and other substances unwanted by the body find their way into urine for subsequent removal from the body. Urinalysis is the testing of the composition and amounts of waste substances in urine, and provides a tremendously powerful diagnostic tool for the medical profession. In particular, many of these substances are indicative of certain medical conditions or other substances which have been metabolized by a person's kidneys.

Using current urinalysis techniques, unwanted substances in a urine sample can mask existing medical conditions, while still some others can masquerade as non-existent medical conditions. In each instance, these unwanted substances undermine the usefulness of urinalysis as a medical diagnostic tool. Some of the unwanted substances that find their way into a urine sample are drugs (both legal and illegal) and metabolites thereof, along with other chemical residues or contaminants that may be present or otherwise contacted during the handling procedures. These substances can disturb the sensitive tests, making the actual state of the body difficult or impossible to determine.

For example, urea compounds, uric acid, insulin levels, para-aminohippuric acid, phenol sulfonphthalein, phosphate, arylsulfatase-A, lysosome, urine amylase, total urine estrogens, specific estrogens, progestins, aldosterone, catecholamines, 5-hydroxyindoleacetic acid, cortisol, homovanillic acid, human chorionic gonadotrophin, creatine, bilirubin, hemoglobin, hydroxyproline, melanin, porphorins, total protein, acid mucopolysaccharide, copper, glucose oxidase and urine ketone can all influence the results of most standard urinalysis testing methods in unintended or unpredictable ways.

Essentially, these testing methods include a variety of immunoassays or assays by other techniques, such as isolation followed by gas or liquid chromatography followed by mass spectrometry. These tests make urinalysis a powerful diagnostic tool for identifying a whole range of conditions. For example, substance abuse and other indicia of disease or bodily state can easily be detected by urinalysis. However, in order to accurately establish standards of comparison for such tests, reliable urine samples are needed which are entirely free from any of the aforementioned substances. Thus, the development of a suitable, synthetic urine substitute would improve testing methods by providing researchers, potential urine donors and testing technicians with an accurate baseline reading for "clean" urine samples to compare against other suspect samples.

To illustrate, a method for detecting this compound is described in U.S. Pat. No. 5,036,014, issued to Elsohly et al., where various deuterated cannabinoids are synthesized to help determine the quantitative amount of tetrahydrocannabinol in a urine sample. One method in particular involves spiking a clean urine sample with known amount of deuterated tetrahydrocannabinol and analyzing the resultant sample with gas chromatography/mass spectrometry in order to establish set standards of comparison. However, a failure to possess a truly clean sample could substantially influence and negatively affect the results of these methods.

Another example of the problems created by interfering chemicals in urine is exemplified by the case of ibuprofen. Ibuprofen is a prostaglandin synthetase inhibitor that may be taken in large doses to relive pain and inflammation characteristic of arthritis. When a patient taking these massive doses is subjected to urinalysis, it may mask other drugs being taken by the donor, or may even be mistaken for tetrahydrocannabinol (a metabolite which many testing technicians classify as being indicative of marijuana use).

Any misidentification of controlled substance use/abuse, personal information (pregnancy, use of cigarettes, etc.) or any of the numerous medical conditions that can be determined using urinalysis can have devastating personal consequences for the urine donor. Thus, some companies sell inexpensive home testing kits in order to provide some level or reassurance to potential urine donors whether they may have such a misidentification. However, given the potential liability for a misidentified or positive test, many lay persons feel intimidated by testing procedures, and these persons would welcome the ability to utilize a known sample, free from unwanted or unknown substances, for the sake of comparison.

In response to the need for a reliable source of relatively inexpensive, "clean" urine samples which are free from any unwanted or unknown substances, numerous attempts to formulate synthetic urine have been made. For example, U.S. Pat. No. 6,306,422 to Batich et al. (table 3, col. 16, line 50 et seq.), U.S. Pat. No. 5,328,954 to Sarangapani (table 1, col. 9, line 29 et seq.), U.S. Pat. No. 5,489,281 to Watanabe et al. (col. 12, example 6) and U.S. Pat. No. 4,146,644 to Griffith et al. (table 1, col. 10). However, none of these references appears to address a simple composition which can be manufactured in an inexpensive manner that contains urea or can be supplemented with urea, and has shelf-stability from use of biocides.

Additionally, all of these references require the use of creatinine or other compounds which can be consumed by bacteria present in the sample. Accordingly, all of these samples will undergo sepsis unless they are immediately used, thereby making these compounds unattractive candidates for mass production and/or consumer sales.

SUMMARY OF THE INVENTION

It is an object of this invention to provide a reliable source of urea-based synthetic urine, along with a method for its manufacture, which is free from any and all unwanted or unknown substances.

It is a further object of this invention to provide a urea-based synthetic urine, along with a method for its manufacture, which is capable of retaining its viability and utility for extended periods of time, for example with use of biocides.

Still further uses for such a synthetic urine can and will be devised by a prospective user based upon his or her own personal disposition, interests and privacy concerns.

Accordingly, a composition of synthetic urine is claimed. This composition includes water, having a pH between about 3 and about 10 with creatinine and biocide. A urea compound is provided in conjunction with the synthetic urine solution. The urea may be dissolved at the time of manufacture and/or prior to testing of the synthetic urine. The composition further includes any compound which dissolves and dissociates in a water solution in a manner which insures that the specific gravity of the resulting solution mixture is between about 1.005 g/cm$^3$ and about 1.025 g/cm$^3$.

The addition of a urea compound, either during manufacture or at a later time, is another element of the invention, and those skilled in the art will readily identify appropriate specific types of biocide oxiders, organics or in situ agents, along with a host of carbonates, halide salts, hydroxide salts and other chemicals which could serve as ideal ionic compounds within the meaning of the invention.

A method for manufacturing synthetic urine involves providing water, dissolving creatinine and biocide in the water, adjusting the resulting solution's specific gravity to be between about 1.005 g/cm$^3$ and about 1.025 g/cm$^3$ and, if necessary, adjusting the pH level of the solution. A urea compound is provided in conjunction with this synthetic urine solution. In another aspect, a method for manufacturing synthetic urine involves providing water, dissolving creatinine and a biocide in the water, adjusting the resulting solution's specific gravity to be between about 1.005 g/cm$^3$ and about 1.025 g/cm$^3$ and, if necessary, adjusting the pH level of the solution, and adding the urea compound at a subsequent time, for example, prior to testing the synthetic urine. Alternatively, the urea compound is dissolved in the synthetic urine solution during manufacturing.

In another aspect, the method contemplates providing water with a pH between about 3 and about 10, mixing creatinine and at least one dissociating ionic compound to adjust the specific gravity of the resulting solution to be between about 1.005 g/cm$^3$ and about 1.025 g/cm$^3$ and removing bacteria from the solution so as to avoid sepsis of the creatinine. A urea compound is provided in conjunction with this synthetic urine solution for subsequent addition to the solution. Alternatively, the urea compound is dissolved in the synthetic urine solution.

In each of these embodiments the same types of biocides, urea compounds, and ionic compounds can be used as were identified in the composition embodiments above.

DETAILED DESCRIPTION

While human urine may at varying times reflect a wide range of chemical compounds, current urinalysis relies upon observation of four basic traits: pH level, specific gravity, the presence of creatinine, and the presence of urea. Consequently, it was discovered that an effective, yet cost efficient, synthetic urine solution having a final specific gravity between about 1.005 g/cm$^3$ and about 1.025 g/cm$^3$ needed only to contain four basic components: water with a pH between about 3 and about 10; creatinine; some means for controlling or eliminating the unwanted sepsis of the creatinine; and some means for controlling the amount of urea. For example, sepsis control/elimination is most readily accomplished through the use of a biocide.

Examining each of these four traits separately, the need for a water-based solution should be apparent. However, it is significant to note that human urine can display a wide range in terms of pH variation, anywhere from about 3 to about 10. This variation can be attributed to any number of factors regarding regional water quality, metabolic idiosyncrasies displayed by each individual and the like. Thus, the water supplied for the composition and method may need to have its pH adjusted accordingly. Significantly, while use of distilled, deionized water will produce the most reliable synthetic urine solutions in terms of elimination of unwanted substances, the invention may be practiced with equal efficacy using distilled water, deionized water or even regular tap water (drawn from any fresh water source having an appropriately low specific gravity, as discussed below). Unless specifically noted to the contrary, use of the term "water" throughout this specification and appended claims is intended to embrace the broadest array of appropriate water sources available.

Urea, also referred to as carbamide, is produced by the body after metabolizing protein. A urea compound is produced when the liver breaks down protein or amino acids, and ammonia; the kidneys then transfer the urea from the blood to the urine. A person can excrete 30 grams of urea a day, mostly through urine, but a small amount is also secreted in perspiration. Urea can also be naturally produced by other mammals, such as certain reptiles and amphibians. Synthetic versions of the chemical compound can be created in liquid or solid form. Unless specifically noted to the contrary, use of the term "urea compound" throughout this specification and appended claims is intended to embrace the broadest array of appropriate urea compound sources available.

The final synthetic urine solution must also have a specific gravity between about 1.005 g/cm$^3$ and about 1.025 g/cm$^3$. Insofar as specific gravity is a measure of relative ionic content of a solution, it should be apparent to those familiar with body chemistry or kidney functioning that certain ions and compounds will be commonly found in human urine, especially those commonly encountered in food and water sources (for example, sodium, potassium, chloride, etc.). In contrast, other elements will be inherently unwise choices at anything beyond a trace level (for example Lanthanoid and Actinoid series ions). The precise amount of the particular compound or compounds selected to adjust the specific gravity will depend directly on the concentration of the particular compound or compounds (if in solution), the molecular weight of its constituents, water temperature, relative volume of water solvent being used and other similar factors. With respect to the water used to manufacture the synthetic urine of the present invention, it is anticipated that significant increases will need to be made to the specific gravity, as distilled, deionized water has a specific gravity of 1.000 g/cm$^3$ and tap water, while likely to vary by region, has a specific gravity around 1.003 g/cm$^3$.

In terms of the best compounds to utilize in adjusting the specific gravity, the single most important trait is that the compound must dissociate when dissolved in water. Additionally, it is preferred to find an inexpensive, widely available compound so as to minimize production costs. To that end, it is believed that carbonate salts, halide salts, hydroxide salts and certain bromides will have particular applicability. By way of illustration rather than limitation, these salts might include sodium bicarbonate, sodium, potassium, magnesium or calcium chlorides; sodium, potassium, or calcium hydroxides; and other similarly inexpensive and widely available salts.

Creatinine is a protein created in connection with muscular activity. As such, medical science recognizes creatinine as an important constituent in the human bloodstream and, to the extent that the kidneys cleanse and purify the bloodstream, in the waste stream expelled from the kidneys in the form of urine. Significantly, because creatinine is a protein, it is the subject of sepsis and decomposition. Thus, creatinine serves as an excellent indicator in urinalysis because it is indicative of human origin and, by virtue of its septic disposition, creatinine also provides a natural measure to determine whether or not a sample was, in fact, recently produced.

In order to insure stable creatinine levels in synthetic urine, it is therefore essential to remove or control the presence of sepsis-causing bacteria. However, whatever method of control is applied must also not interfere with the processes underpinning most urinalysis techniques. Thus, the use of an appropriate biocide is absolutely critical to the efficacy of the synthetic urine. To the extent that human urine is sterile when excreted (under normal body conditions), the use of biocide represents a distinct departure from previous approaches to the manufacture of synthetic urine which relied solely on mimicking the compounds in actual urine without any regard for the long-term shelf life of the synthetic solution. Moreover, it further demonstrates the need to select a biocide which is biologically active, yet does not interfere overtly with the chemistry of the synthetic urine solution itself (either through its chemical signature or by virtue of an abnormally large amount being detectable in the solution).

A biocide can be generically defined as a substance used to control or eliminate microbial populations in a sample. Generic examples of biocides that have particular applicability when used in connection with the present disclosure include, but are not limited to the following: oxidizing biocides, organic biocides, and a somewhat more generalized category referred to as in situ agents. Non-limiting examples will be discussed briefly below, although it should be understood that biocides are a term of art, known to those familiar with water chemistry processes.

Oxidizing biocides are generally self explanatory. This class includes any biologically effective agent which relies upon an oxidation process, including but not limited to various peroxides, hypochlorites, bromides and super oxides. Organic biocides encompass an expansive list of proteins and cyclical compounds known to those skilled in the art. In situ agents can be chemical compounds or actual physical processes designed to kill bacteria in a manner which is either self-generating or effective enough to prevent future degradation of the urine. Generic examples of such in situ agents include ozone, chlorine dioxide (or other dioxides), and ultraviolet radiation or irradiation processes followed by hermetic sealing of the sample.

Specific examples of various biocides contemplated above include: BHAP (such as 2-Bromo-4-hydroxyacetophenone, an organo-bromine group); Bronopols (such as 2-Bromo-2-nitropropane-1,3 diol, an organo-bromine group); Carbamates (such as a mix of sodium dimethyldithiocarbamate (DIBAM) and disodium ethylene bisdithiocarbamate (NIBAM), or single product, such as potassium n-hydroxymethyl-n-methyldithiocarbamate, an organo-sulfur group); Chlorothioether (such as 2,2 Dihydroxy-5,5-dichlorodiphenyl monosulfide, a chlorinated phenolic thioether); DBNPA (such as 2-2-Dibromo-3-nitrilopropionamide, an organo-bromine group); DTEA, DTEA II (such as 2-(Decylthio)ethanamine, an alkylthioamine group); Guanides (including Guanidine and Biguanides) (such as dodecylguanidine hydrochloride and acetate, also polyhexamethylene biguanide hydrochloride, and tetradecylguanidine, all aliphatic guanadines); Glutaraldehydes (such as Pentane-1,5-dial., an aldehyde group); Isothiazolines (such as Alkyl isothiazolin-3-ones, an organo-sulfur group); MBT (such as Methylene bis(thiocyanate), an organo-sulfur group); Polyquats (such as broad-spectrum, cationic polymers of low molecular weight); Quats (ADBACs) (such as Alkyldimethylbenzylammonium chloride (also known as alkylbenzyldimethyl ammonium chloride or benzalkonium chloride), a quaternary ammonium compound group); Sulfones (such as Bis(trichloromethyl) sulfone, an organo-sulfur group); TBTO (such as Bis(tributyltin)oxide, an organo-tin group); TBZ (Tertbuthylazine) (such as 2-(tert-butylamino)-4-chloro-6-(ethylamino)-s-triazine, a Triazine group); TCCBN (such as Tetrachloro-2,4,6-cyano-3-benzonitrile, TCCBN functions similarly to the chlorophenols); TCMTB (such as 2(thiocyanomethylthio) benzothiazole); Thiones (such as Tetrahydro-3,5,dimethyl-2H-1,3,5-thiadiazine-2-thione, an organo-sulfur group); THPS (TKHPS) (such as Tetrakish(hydroxymethyl)phosphonium sulfate, an alkyl phosphonium group); and TTPC (such as Tributyltetradecylphosphonium chloride, an alkylphosphonium group). Additionally, with respect to more commonly understood items, such as peroxides, hypochlorites and the like, it should be understood that this specification encompasses all forms of such compounds (for example, hydrogen peroxide, sodium peroxide, sodium hypochlorite, potassium hypochlorite, etc.). Other examples of biocides may exist and various exemplary embodiments are encompassed within this specification.

Notably, as embraced by this disclosure, oxidizing biocides, and hypochlorite in particular, should not be confused with the agents that are employed to oxidize metabolites in urine samples. Such metabolite oxidizers are often referred to as "adulterants" within the urinalysis industry. Adulterants are substances deliberately added to actual urine samples to chemically alter the metabolites indicative of certain conditions so as to render these metabolites undetectable by standard urinalysis techniques.

Even though some substances like hypochlorite may possess utility as both a biocide and as an adulterant, the intended use of that substance (as either a biocide or a metabolite oxidizer) will substantially influence the conditions, concentration and manner in which the substance is provided. In particular, use as a biocide requires smaller concentrations and little to no regard for when the biocide is added during the manufacturing process. To illustrate, an oxidizing biocide such as sodium hypochlorite can be added in amounts as small as 1 mL per 3.8 L of water. Similar concentrations of other oxidizing biocides will have equal efficacy, as recognized by those skilled in the art.

In contrast, use of hypochlorite as an adulterant as taught, inter alia, in U.S. Pat. No. 6,861,262 must occur at higher concentrations and in a specific manner so as to oxidize certain metabolites or compounds. Thus, hypochlorite (and other oxidizing biocides) found in the present solution prevents the unwanted growth of bacteria. Moreover, to the extent that adulterants are often added to actual urine samples, the composition of the resulting mixture is substantially more complex, in terms of the variety of chemical species present, than the simplified composition of the present invention.

Another aspect of the present urine solution relates to the addition of urea in some form to the synthetic urine sample. Urea or carbamide is an organic compound with the chemical formula $CO(NH_2)_2$. Urea serves an important role in the metabolism of nitrogen-containing compounds by animals and is the main nitrogen-containing substance in the urine of mammals. Urea compounds can be produced from inorganic starting materials. Examples of urea compounds include, but are not limited to, carbamide peroxide, allantoin, and hydantoin.

Urea is increasingly being tested for in urinalysis techniques. Its presence within synthetic urine could add an additional level of realism for some applications. For example, the addition of urea to synthetic urine may serve as a scent producing material to make the synthetic urine appear more natural. Notably, to the extent that urea is provided, it will need to be considered in the calculations of the amount of ionic dissociating compounds required to adjust the specific gravity and/or pH to the desired levels. Urea compounds can be dissolved in the water solution or synthetic urine solution. As an optional addition, a sugar may be dissolved with the urea.

Providing a shelf stable synthetic urine with a biocide having a kill factor for a specified period, such as 1-2 years, will keep the product sterile. Although 1-2 years is specified, this is a non-limiting example of a kill factor time period. Other desired time periods may be optimal. The urea compound may be added to the water or synthetic urine preferably just prior to testing of the urine. In an embodiment, the urea compound is added to the water or synthetic urine during manufacture. A shelf stable synthetic urine with biocide can be placed in the US and other markets around the world. Similarly, the synthetic urine is formulated for use by various customers in these varying locations.

Other functionally inconsequential additives or steps may also be included without departing from the principles of this invention. While these additives and steps expressly cover all foreseeable equivalents of the elements recited above, additional variations are possible. For example, it is possible to include a coloring agent and or olfactory substance to enhance the aesthetics or apparent authenticity of the synthetic urine produced according to this invention.

The foregoing detailed description has been given for clearness of understanding only and no unnecessary limitations should be understood therefrom as some modifications will be obvious to those skilled in the art without departing from the scope and spirit of the appended claims.

I claim:

1. A synthetic urine solution comprising:

water having a pH between about 3 and about 10;

creatinine and a biocide, said creatinine and biocide dissolved within said water to form a solution exhibiting a specific gravity and said creatinine and biocide selected in relative concentrations to minimize sepsis;

at least one dissociated ionic compound also dissolved within said solution to adjust the specific gravity of the solution to between 1.005 g/cm$^3$ and 1.025 g/cm$^3$; and at least one urea compound provided in conjunction with the synthetic urine solution, wherein the at least one urea compound is carbamide peroxide, and optionally allantoin and optionally hydantoin.

2. The synthetic urine solution of claim 1, wherein the at least one urea compound is either dissolved within said solution or provided separately to be dissolved within said solution at a subsequent time.

3. The synthetic urine solution of claim 1, wherein said at least one ionic compound is selected from at least one of carbonate salts, halide salts, hydroxide salts, and bromides.

4. A method of manufacturing a synthetic urine solution comprising:

providing water;

dissolving creatinine and biocide into said water to form a solution exhibiting a specific gravity level, said creatinine and biocide being selected in relative concentrations to minimize sepsis;

adjusting said specific gravity level of said solution to between 1.005 g/cm$^3$ and 1.025 g/cm$^3$; and providing at least one urea compound in conjunction with the synthetic urine solution, wherein the at least one urea compound is carbamide peroxide, and optionally allantoin and optionally hydantoin.

5. The method of claim 4, wherein the at least one urea compound is either dissolved within said solution or provided separately to be dissolved within said solution at a subsequent time.

6. The method of claim 4 further comprising sealing said synthetic urine solution within a container so as to further minimize sepsis of said synthetic urine solution.

7. The method of claim 4, further comprising the step of adjusting the pH level of the solution between about 3 and about 10.

8. A method of manufacturing a synthetic urine solution comprising:

providing water having a pH between about 3 and about 10;

dissolving creatinine and at least one dissociating ionic compound in the water to form a solution exhibiting a specific gravity, said creatinine and at least one dissociating ionic compound selected in relative concentrations to adjust said specific gravity to between 1.005 g/cm$^3$ and 1.025 g/cm$^3$;

adding a biocide into said solution;

removing bacteria from said solution;

and providing at least one urea compound in conjunction with the synthetic urine solution, wherein the at least one urea compound is carbamide peroxide, and optionally allantoin and optionally hydantoin.

9. The method of claim 8, wherein the at least one urea compound is either dissolved within said solution or provided separately to be dissolved within said solution at a subsequent time.

10. The method of claim 9 wherein the step of dissolving creatinine and at least one dissociating ionic compound also includes dissolving the at least one urea compound in the water, said at least one urea compound selected in a concentration relative to that of said creatinine and at least one dissociating ionic compound so as to maintain the specific gravity of the solution between 1.005 g/cm$^3$ and 1.025 g/cm$^3$.

11. The method of claim 10, further comprising the step of sealing said synthetic urine solution within a container.

12. The method of claim 8, further comprising the step of sealing said synthetic urine solution within a container.

13. The method of claim 8, wherein the bacteria are removed from said solution using an in situ agent selected from at least one of ozone, dioxides, ultraviolet radiation, and irradiation processes followed by hermetic sealing of the solution.

* * * * *